(12) United States Patent
Lowry et al.

(10) Patent No.: US 6,827,476 B2
(45) Date of Patent: Dec. 7, 2004

(54) SYSTEM FOR CONTROLLING MIXING PROCESSES

(75) Inventors: Stan Lowry, Kernersville, NC (US);
Garcie McCall, Germanton, NC (US);
Richard B. Batté, Pfafftown, NC (US)

(73) Assignee: HDN Development Corporation, Florence, KY (US)

(*) Notice: Subject to any disclaimer, the term of this patent is extended or adjusted under 35 U.S.C. 154(b) by 0 days.

(21) Appl. No.: 10/670,450

(22) Filed: Sep. 24, 2003

(65) Prior Publication Data

US 2004/0062841 A1 Apr. 1, 2004

Related U.S. Application Data

(62) Division of application No. 09/852,534, filed on May 10, 2001, now Pat. No. 6,656,515.
(60) Provisional application No. 60/203,362, filed on May 10, 2000.

(51) Int. Cl.[7] .............................. A21C 1/00; B29B 7/00
(52) U.S. Cl. ........................ 366/97; 366/100; 366/142; 366/206; 366/601
(58) Field of Search ........................... 366/97, 98, 100, 366/142, 206, 601; 99/348, 327; 426/231, 519, 549

(56) References Cited

U.S. PATENT DOCUMENTS

| | | |
|---|---|---|
| 1,279,143 A | 9/1918 | Patterson |
| 4,492,713 A | 1/1985 | Chauvin |
| 4,747,690 A | 5/1988 | Hayashi |
| 4,766,766 A * | 8/1988 | Ahlert et al. ............... 426/231 |
| 5,472,273 A | 12/1995 | Fowler et al. |
| 5,556,198 A | 9/1996 | Dickson, Jr. et al. |
| 5,562,020 A * | 10/1996 | Shigeshiro .................. 366/601 |
| 6,161,954 A | 12/2000 | DeWall |

FOREIGN PATENT DOCUMENTS

| | | |
|---|---|---|
| DE | DD 217697 A1 | 1/1985 |
| JP | 61219333 | 9/1986 |
| JP | 05056744 A | 3/1993 |

OTHER PUBLICATIONS

PCT/US01/15060 International Search Report, mailed Dec. 3, 2001.

* cited by examiner

Primary Examiner—George C. Yeung
(74) Attorney, Agent, or Firm—Kilpatrick Stockton LLP

(57) ABSTRACT

In a method for controlling the mixing of dough ingredients in a mixer, dough ingredients are mixed. The amount of power supplied to the mixer is measured in specified time intervals. Data relating to the amount of power supplied are stored. Based on the stored data, a decline in the amount of power supplied to the mixer is identified and the mixer mixes the dough ingredients for a predetermined period of time after the decline is identified. A mixer of the present invention includes a mixing device, a motor coupled to the mixing device, a power source coupled to the motor, and a mixing-time controller.

20 Claims, 3 Drawing Sheets

FIG. I

SYSTEM FOR CONTROLLING MIXING PROCESSES

CROSS-REFERENCE TO RELATED APPLICATIONS

This application is a divisional of U.S. patent application Ser. No. 09/852,534, filed May 10, 2001 now U.S. Pat. No. 6,656,515, which is incorporated in full by reference, and which claims the benefit of and incorporates in full by reference U.S. Provisional Patent Application Ser. No. 60/203,362, filed May 10, 2000, entitled "Method and System for Controlling the Mixing Process of a Subject Product."

FIELD OF THE INVENTION

The present invention generally relates to mixers and systems for controlling mixing. The mixers may be utilized in industrial and commercial settings for mixing ingredients, such as dough ingredients. An embodiment of the present invention relates to controlling the mixing of product mix, such as doughnut mix.

BACKGROUND

In making high-quality doughnuts, it is very important to use a dough that has been mixed for an optimum amount of time. If the dough ingredients are mixed for too short or too long of a period of time, the resulting doughnut will not have a taste that is of the highest quality and that meets the standards of discerning consumers.

Dough mix that is used to make doughnuts is made up of a variety of materials. The ingredients in such dough mix include yeast, water, and flour. Conventionally, various vendors provide yeast and flour to a maker of doughnuts. The quality, make-up, and characteristics of the ingredients, most notably the flour, will vary somewhat from year to year, from vendor to vendor, and sometimes from shipment to shipment. For example, the quality of flour may vary from crop-year to crop-year, depending on the weather and other variables.

Conventionally, the decision as to the length of time a dough mix should be mixed in a mixer to obtain a high-quality doughnut is made by an individual with many years of experience in the field. Essentially, such a decision is an art, and such an individual would examine dough mix before, during, and after mixing during several mixing runs before making such a decision. Based on the individual's visual and tactile examination of the dough mix, the individual would decide the length of time that the dough mix should undergo mixing during a particular time period (e.g., that year). The individual would choose the length of mixing time for optimum development of the dough mix to produce an optimum doughnut. For example, the individual may choose a time period between twelve and fifteen minutes as an optimum mixing time for a particular year. It is conventionally recognized that this optimum development of the dough mix occurs approximately two to four minutes after the dough mix reaches its peak development (i.e., the point in its development at which the dough mix reaches its optimum extendability).

The length of time selected by such an individual depends on a great number of factors, including the person's past experience and judgment. Thus, the length of time selected may vary from experienced individual to experienced individual. Moreover, the length of time selected by an individual may vary from year-to-year, depending on the characteristics of the materials used during a particular time period. The length of time selected may also vary depending on the relative make-up of the mix, e.g., the ratio of water to other materials, the temperature of the mix, and other factors (e.g., RPM of the mixing machine).

In a large retail doughnut operation with multiple retail stores, a very high volume of dough mix is used. Due to time, costs, administrative, and other constraints, mixing-time selection is conventionally made only once or twice by a skilled individual during a year in a large operation with multiple stores. Thus, in such an operation, the mixing-time selection made may not be optimum for every dough mix shipment, but is considered generally optimum on average for the shipments used during a year. Of course, given the variation in dough mix characteristics that may occur, one complication with the conventional method is that the mixing-time selected may be optimum or near-optimum for the great majority of dough mix shipments, but departs from optimum or near optimum for some of the shipments.

In such a large operation, too, the dough mix is distributed to the various retail stores in the operation and is mixed by employees of the retail stores according to instructions provided using on-site mixers. One of the instructions provided to the retails stores is the percentage amount of water to add to the dough mix (the water portion is generally not included in the delivery of dough mix) and the length of time that the dough mix should be mixed after adding water. The employees of the retail store may not, for one reason or another, follow the instructions provided exactly as provided. For example, more or less water than specified in the instructions may be added. A variation in water added will vary the make up of the dough mix, and will cause the optimum mixing time for that particular batch to vary from the length of time specified in the instructions. For example, the addition of less than the specified amount of water may cause the mixing time required to result in a doughnut of high quality to change. Thus, if an employee of a retail store adds less than the specified amount of water, but continues to mix the dough mix for the specified amount of time, a less-than-optimum dough is produced. Likewise, if the employee varies the amount of mix time while using the specified mix ratios, a less-than-optimum dough may be produced.

Thus, a complication of the conventional method includes the application of a single mixing-time to a high volume of dough mix shipments in a large, retail doughnut sales operation. Another complication is that producing optimum dough depends on employees of a retail store following the specific instructions provided with dough mix shipments.

A method and system for mixing dough mix that results in optimum dough for producing high-quality doughnuts that has none of, or fewer of, these complications is needed.

SUMMARY

The present invention includes methods and systems that control the mixing process of a subject product such that the product is automatically mixed to a desirable level. An example of a suitable subject project for mixing using the present invention is dough used in making doughnuts and similar products.

In one aspect, the present invention provides a mixer comprising a motor, a power source, a mixing apparatus, a mixing time controller including a power meter, a processor and a timer, wherein the timer and the power meter are in communication with the processor. Suitable motors for use in a mixer of the present invention include motors conventionally utilized in industrial mixers, e.g. electric motors, DC motors, AC motors, and the like.

The mixing apparatus may comprise a dough hook, agitators, paddle, spoon, or other mixing apparatus conventionally utilized to mix dough. The power source of a mixer of the present invention should provide sufficient power to power the motor. The power source may be a source of AC or DC current. An example of a suitable power source is a 220 Volt AC power source.

In an embodiment of a mixer of the present invention, motor operation is controlled by a mixing-time controller. In an embodiment, the mixing-time controller comprises a switch to halt the motor and stop the mixing apparatus from mixing the dough.

In another embodiment, the mixing-time controller further includes a power meter and a processor. The power meter measures the power consumption of the motor. The processor processes information from the power meter and the timer, and calculates when to halt mixing based on such information.

In an alternative embodiment, the motor includes a transmission and/or a clutch between the motor and the mixing apparatus. The mixing-time controller may include a switch for disengaging the clutch or otherwise halting the mixing apparatus to stop dough mixing.

In an embodiment of a method of the present invention for controlling the mixing of dough ingredients, dough ingredients are mixed in a mixer. Examples of conventional dough ingredients include flour, yeast and water. A mixing-time controller having a power meter, a processor, and a timer is provided in a mixer having a mixer motor and a power source. The amount of power supplied to the mixer motor is measured in specified time intervals. For example, the amount of power being supplied may be measured every second using the power meter. Data relating to the amount of power supplied are stored. As the data are stored, a processor analyzes the data to identify a decline in the amount of power supplied. A control algorithm preprogrammed in the processor may be used to identify the decline. A decline in the amount of power supplied indicates that the dough is nearly mixed to a desired consistency. Once this decline in the amount of power supplied is identified, it is desirable to continue to mix the dough for a predetermined period of time. An example of a predetermined period of time is two minutes.

A timer may be used to measure the predetermined period of time. The timer may be activated by a signal sent from the processor after the identification of the decline in the amount of power supplied. After the predetermined period of time has elapsed, power is no longer supplied to the mixer motor, thus stopping the mixing of the subject dough mix.

In a further embodiment, the data relating to the amount of power supplied at the specified time intervals are sent to a computer for storage and further analysis. The data may also be sent over a computer network.

Embodiments of the present invention offer a wide variety of advantages and features. One advantage and feature is that embodiments detect the peak development point for a batch of mix, rather than using a pre-set time period.

Another advantage and feature is that, in embodiments, dough mix is mixed for an optimum amount of time for the production of high-quality doughnuts.

Moreover, an advantage is that the mixing time of a batch of mix is conducted based on the make-up of that particular batch.

A further advantage and feature is that labor cost is lessened by using embodiments of the present invention.

A still further advantage and feature is that embodiments avoid the application of a single mixing time to a high volume of dough mix shipments in a large, retail doughnut sales operation.

A still further advantage and feature is that the production of optimum dough mix is less dependent on employees of a retail store following the specific instructions provided with dough mix shipments.

Additional uses, objects, advantages, and novel features of the invention will be set forth upon review of the attached exhibits and in the detailed description that follows, and will become more apparent to those skilled in the art upon examination of the following.

DETAILED DESCRIPTION

The present invention includes methods and systems that control the mixing process of a subject product such that the product is automatically mixed to a desirable level. An embodiment of the present invention that may be used to produce high-quality doughnuts is described herein. For example, the present invention may be used to mix dough ingredients (e.g., flour, yeast and water) to form dough for making doughnuts.

Figure 1:
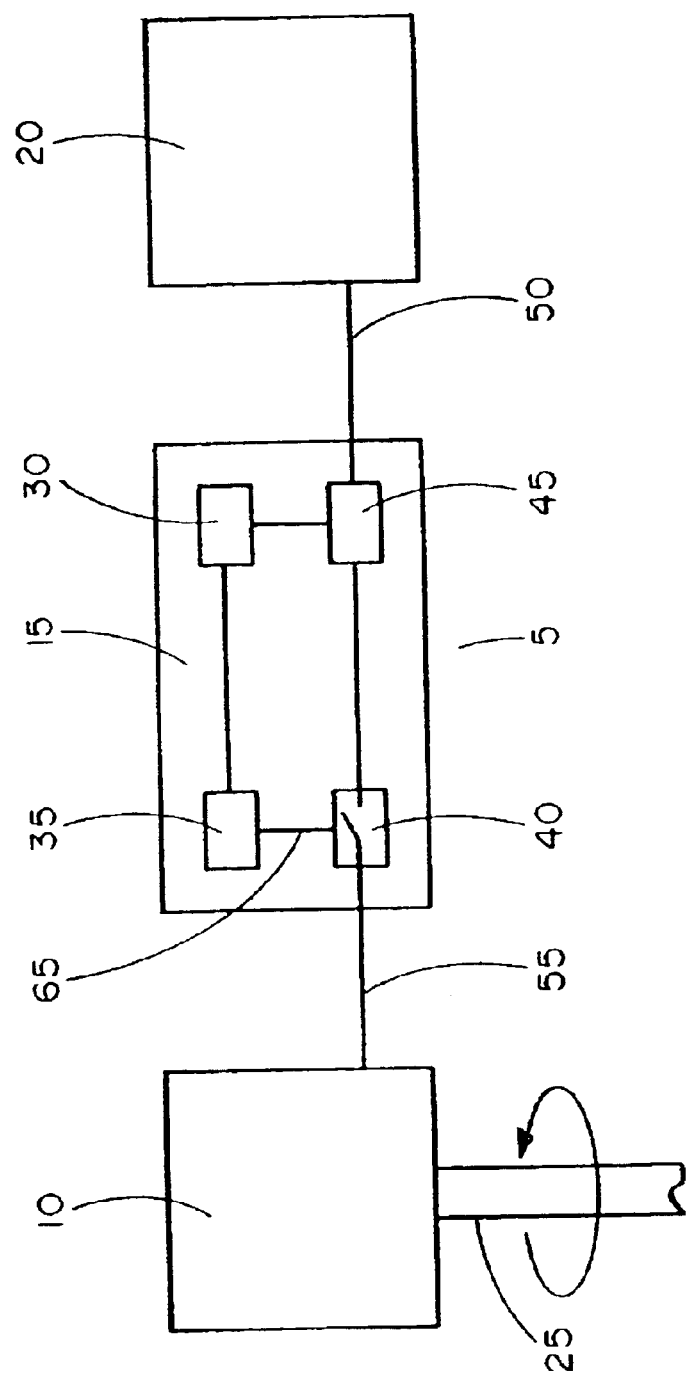
FIG. 1 illustrates an embodiment of a system of the present invention for controlling the mixing of dough ingredients.

Referring to FIG. 1, an embodiment of a dough mixing system 5 according to the present invention that is used in mixing dough ingredients in the production of doughnuts is shown. The system 5 comprises a mixer motor 10, a mixing-time controller 15, and a power source 20. Those of ordinary skill in the art will recognize that the mixer motor 10 and the power source 20 are those that are included in dough-mixing machines conventionally used to mix dough mix, and that the mixer motor and power source used depends on the size of the machine, its volume and power rating, and other factors. Examples of a mixing machine, including such a mixer motor 10 and power source 20, include the Welbuilt Varimixer W60 and the Magna Mixers Magna Mixer Triumph 1/4 BBI.

The mixer motor 10 is connected to a mixing rod 25, which is rotated by the mixer motor 10. The mixing rod 25 is connected to a mixing device, such as dough hooks, agitators, mixing paddles or spoons (depending on the machine used), which are placed into a mix of dough ingredients. When the mixing device is rotated in the dough mix by the mixer motor 10, the mixing device mixes the dough ingredients. When the dough mixing system 5 is in operation, excluding start-up acceleration and stop-point deceleration, the mixer motor 10 rotates the mixing rod 25 at approximately constant speed.

The mixing-time controller 15 shown includes a processor 30, a timer 35, a switch 40, and a power meter 45. The power source 20 provides power to the mixer motor 10. A power line 50 connects the power source 20 to the mixing-time controller and the power line 50 is connected to the power line 55 which connects to the mixer motor 10. The mixing-time controller 15 shown is connected in series between the power source 20 and the mixer motor 10. Specifically, the power meter 45 and the switch 40 are connected in series between the power source 20 and the mixer motor 10.

The power source 20 may be an AC or DC power supply. The power source 20 shown provides AC power at a constant voltage. The current supplied by the power source 20 to the mixer motor 10 through the power lines 50, 55 varies depending on the amount of power needed by the mixer motor 10 to maintain an approximately constant speed. The more torque that is needed to mix the dough mix at a particular time, the more power and thus the more current that is needed at that time. Likewise, when less torque is needed to mix the dough mix, less power and thus less current is needed. For example, after doughnut ingredients are mixed to the point of peak development, less torque, and thus less power, is needed to mix the ingredients at constant speed. At peak development, the dough may exhibit various characteristics. For example, the dough has reached an optimum extendability, the dough has a dry appearance and the dough has a smooth appearance. At peak development, the dough rides the mixing device as a single mass (i.e., the dough has been mixed such that it is a single mass rather than numerous pieces of dough).

The power meter 45 measures the amount of power supplied by the power source 20 to the mixer motor 10 on the power lines 50, 55. The power meter 45 shown measures the amount of current and voltage on the power line 50. The power meter used must be capable of reading the range of current supplied by the power source 20 to the mixer motor 10. This range of current varies depending on the size and type of mixing system at issue. One important factor is the power rating of the mixer motor. Also, the power meter 45 is capable of outputting data relating to the amount of power being used by the mixer motor 10 on a near-constant basis. Those of ordinary skill in the art will recognize that there are a wide variety of power meters that may be used in such a system 5. An example of a power meter that may be used in an embodiment of the present invention is the Load Control Model VPC10HP.

A processor 30 is connected to the power meter 45 and the timer 35. The power meter 45 outputs data to the processor 30 indicating the amount of power that is being supplied to the mixer motor 10 by the power source 20 at specified time intervals. The power meter 45 may determine the power supplied to the mixer motor 10 two hundred (200) times per second, and output the power data at the same rate. This power-level data is provided to the processor 30 by the data connection 60 between the processor 30 and the power meter 45. The power-level data is received by the processor 30 for analysis as will be discussed below.

The processor 30 receives and stores the power-level data from the power meter 45. The processor 30 is programmed to include a control algorithm (discussed further below). The processor 30 reads the power-level data and applies the control algorithm, the results of which are a function of the power-level data. When the control algorithm is met, the processor 30 sends a trigger signal to the timer 35. The processor 30 includes memory (in the embodiment shown, the processor 30 includes short-term memory having the ability to store power-level data for at least forty seconds). The power-level data, and the time associated with each power-level data point, is stored in the memory of the processor.

In the embodiment shown, the algorithm examines the power-level data to determine the point at which the dough that is being mixed by the mixer motor 10 has reached its peak development. The power needed by the mixer motor 10 to mix dough mix that has reached peak development begins to go down because the dough mix has become easier to mix (e.g., reached optimum extendability). Thus, a decline in the amount of power supplied to the mixer motor signifies that the dough mix has reached its peak development. Once this change is detected, the processor 30 sends a signal to the timer 35, which begins a countdown for a predetermined time period. The system 5 continues to mix for this predetermined period of time after identification of the decline in the amount of power supplied. Once the time period expires, the mixer motor 10 is shut off and the system 5 stops mixing. An example of a suitable predetermined time period is two minutes. The algorithm is discussed further below.

Figure 3:
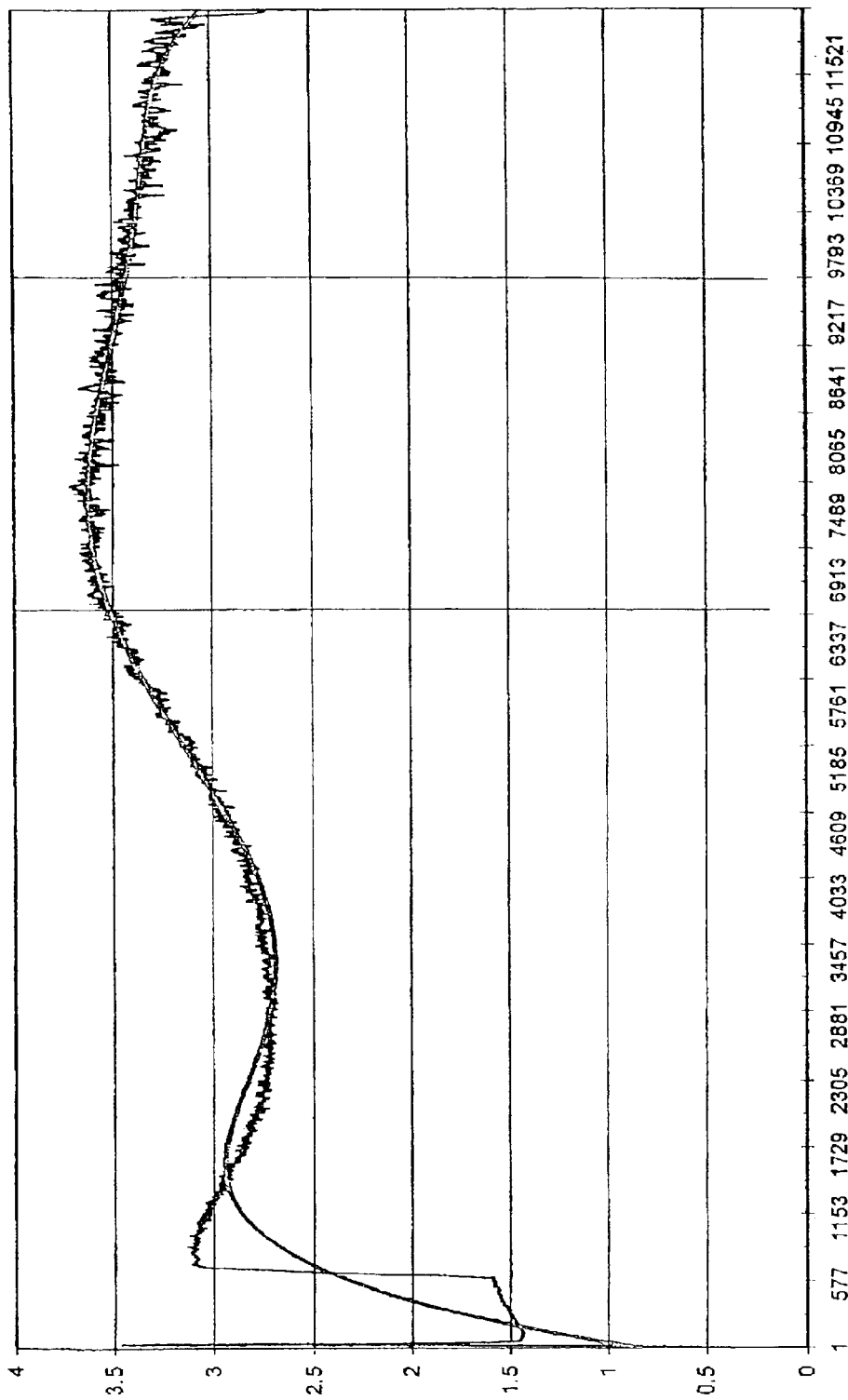
FIG. 3 comprises a sample graph showing mixer motor power use versus time as output from an embodiment of a method and system of the present invention.

An example graph showing mixer motor power use versus time is shown in FIG. 3. As shown in FIG. 3, at approximately 12.5 minutes (data point 7489), there is a significant drop off in power use by the mixer motor. It is desirable for the algorithm to cause the processor 30 to detect the drop off in power use, and to send a trigger signal to the timer 35 at that time.

As mentioned, the timer 35 receives the trigger signal from the processor 30. When the timer 35 receives the trigger signal from the processor 30, the timer 35 activates. The timer 35 is pre-programmed with a timer period (i.e., the timer is set to count down for a particular amount of time). In one embodiment, the timer 35 is programmed with a timer period of two minutes (one hundred and twenty seconds). Though, a range from one minute to four minutes may be desirable. Three minutes may be desirable for a strong mix. The two minute time period is selected as a mid-range selection. Experimentation may reveal a particular timer period that is desirable in a particular application.

In the embodiment disclosed, the system stops mixing after a predetermined period of time has elapsed after the dough has reached its peak development. In other embodiments, the system may continue mixing after the dough has reached its peak development until a condition other than time is met. After the dough reaches peak development (i.e., after a decline in the amount of power supplied to the mixer is detected), the system may begin monitoring another condition, such as dough volume, dough temperature, dough water content, etc., and continue mixing until a particular event occurs. For example, the system may continue mixing until the temperature of the dough changes by a particular amount.

After the timer 35 is activated with a trigger signal from the processor 30, and once the timer period (two minutes) expires, the timer 35 sends a shut-off signal to the switch 40 through a data connection 65. The switch 40 is normally closed allowing power to run from the power source 20 to the mixer motor 10. The shut-off signal causes the switch 40 to open. When the switch 40 opens, the connection between the power lines 50, 55 is open (or broken), and power no longer flows to the mixer motor 10, thus shutting off the mixer motor 10 and stopping the mixing of the dough ingredients. With a two minute timer period, the mixer motor 10 shuts off two minutes after the timer 35 receives the trigger signal from the processor 30. After the mixer motor 10 shuts off, the dough may be removed from the machine and used to make doughnuts.

An algorithm for use in the mixing-time controller 15 is developed for doughnut mix. A variety of algorithms may be selected by the manufacturer or user of a system in accordance with the present invention. In one embodiment, after the dough reaches its peak development (i.e., after a decline in the amount of power supplied to the mixer motor 10 is identified), the mixing may be halted from one to four minutes afterwards, depending on the strength of the mix. By monitoring the power used by the mixer motor 10, the peak development point may be detected.

Thus, in the embodiment shown, an algorithm that detects the peak development point by examining power data measured by the power meter 30 is used. Preferably, the algorithm used in the system 5 comprises an algorithm that allows for spikes and other anomalies in the power-use data.

Those of ordinary skill in the art will recognize that there are a variety of algorithms that may be used to carry out embodiments of the present invention. One example is the comparison of current power usage data to power usage data from thirty seconds previous. An algorithm may compare power usage at a testing time of every five seconds to the power usage thirty seconds previous. Once the algorithm detects that less power is being used by the mixer motor 10 for three consecutive testing times, the algorithm causes the processor 30 to send the trigger signal to the timer 35. By programming the algorithm to cause the processor 30 to send the trigger signal after three consecutive testing times at which less power is being used, the algorithm may avoid premature shut-off of the mixer as the result of a power spike. Recognizing that peak may have been reached fifteen to twenty seconds before the trigger signal is sent due to the algorithm requiring three consecutive testing times of less power usage, the timer's time period may be set for less time (e.g., 100–105 seconds if it is desired to shut down 120 seconds after peak).

An example of another algorithm that may be used is the "time weighted average" approach. This algorithm may examine the last ten power-use data points. The most-recent sample (the tenth sample) is weighted or valued three times more than the first (or most distant in time) sample. For example, its value may be multiplied by three. The next-to-most-recent sample (the ninth sample) is weighted or valued two times more than the first sample. The ten samples (after weighting as described) are then averaged and compared with a weighted and averaged sample taken thirty seconds previously. If the current, averaged sample is less in value than the one taken for the previous thirty seconds, the processor 30 sends the trigger signal to the timer 35. The system 5 continues to mix as the timer 35 counts down for the predetermined period of time.

A controller for use in the present invention is constructed and placed on a circuit board and in a suitable housing. During the construction of the controller, a processor 30 is programmed with the desired control algorithm and a timer 35 is programmed with the desired timer period. The controller may then be installed in a conventional doughnut mixer by placing the controller in the power circuit of the mixing machine as shown in FIG. 1 (and FIG. 2). Afterward, dough ingredients may be placed in the mixer and the machine turned on. After the processor 30 determines that the programmed point has been reached (e.g., a decline in the power supplied to the motor), the processor 30 sends the trigger signal to the timer 35. After the preprogrammed timer period expires, the timer 35 sends a shut-down signal to the switch 40, which opens, thereby shutting off the mixer motor 10. In this way, the dough mix is mixed for an optimal amount of time.

In the system shown in FIG. 1, the timer 35 and processor 30 are shown separately. In other embodiments, the timer 35 may be part of the processor 30, or they may be part of the same structure.

Other embodiments in accordance with the present invention may be used. In other embodiments, the processor includes or is connected to longer-term memory, which records the power-level data supplied by the power meter 45 and the time at which the power-level data is recorded. Likewise, the power meter 45 may include such memory.

The processor 30 may also include additional data output ports (the trigger signal output port that is connected to the timer 35 in FIG. 1 is the first data output port). The processor 30 may output the power-level data using a second data output port. This data output port may be connected to a computer, e.g., a personal computer. The computer may be used, for example, to read and analyze the power-level data. This computer may include a modem, which allows remote terminals access to the data. Similarly, the second data output port itself may be connected to a computer network, giving the network and attached terminals access to the power-level data.

An example of hardware and software that may be used in an embodiment of the present invention includes the following: a Hewlett Packard Vectra VE17, having a 466 Mhz Celeron Processor, 8.4 GB hard drive, 64 MB RAM, Samsung Monitor 550B, Microsoft Windows 95, Microsoft Excel 2000, Microsoft 98 NZCDR, Andantech "Geni DAC" data acquisitioner at 1000 times per minute, Andantech data acquisition card PCL 818L, and an Epson EX880 dot matrix printer.

In other embodiments, the processor 30, as well as the timer 35, may include additional data input ports (a first data input port on the processor 30 is connected to the power meter 45; a first data input port on the timer 35 is connected to the processor 30). The processor 30 and the timer 35 may be programmable (and reprogrammed) via second data input ports. For example, the timer period may be changed in the timer 35, and the algorithm may be changed in the processor 30, using data received in these second data input ports. These second data input ports may be connected to a computer or a computer network.

Preferably, the mixing-time controller 15 is preprogrammed and the time periods and algorithm are not adjustable by an individual located at the individual machine. In other embodiments, though, the system 5 may be constructed with input controls (e.g., digital controllers, mechanical knobs, or other devices) that allow the timer period and pre-selected variables in the processor algorithm to be adjusted manually by an operator of the machine. For example, a digital controller with a key pad may be used to adjust the timer period from two minutes to three minutes by an operator of the machine. As another example, a user may manually override the algorithm and set the mixing time for fifteen minutes.

Figure 2:
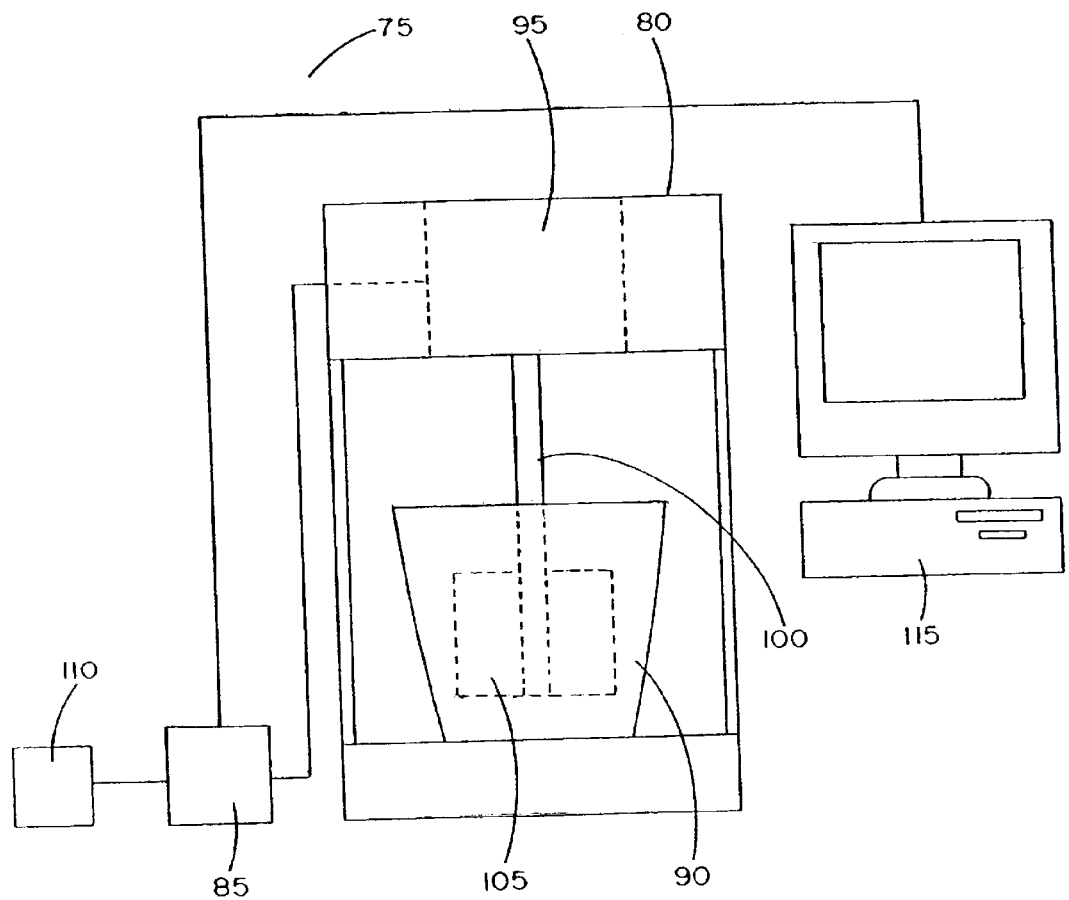
FIG. 2 illustrates an embodiment of a mixing system of the present invention.

FIG. 2 illustrates an embodiment of a system 75 for mixing dough ingredients that incorporates a mixing-time controller 85 with an existing mixer 80. In the embodiment shown, the dough ingredients are mixed in a mixing bowl 90 or similar container. A mixing rod 100 is coupled to a mixer motor 95, which rotates the mixing rod 100. A mixing device 105 is attached to the mixing rod 100 such that as the mixer motor 95 rotates the mixing rod 100, the dough ingredients are mixed by the mixing device 105. The mixing device 105 may be a dough hook (or multiple dough hooks), an agitator (or multiple agitators), a paddle (or multiple paddles) or a spoon (or multiple spoons).

The mixing-time controller 85 is positioned and connected in series between the power source 110 and the mixer motor 95. While the mixing-time controller 85 is shown outside of the mixer 80, the mixing-time controller may also be installed on the interior of the mixer 80, such as near the mixer motor 95. The mixing-time controller 85, among other things, determines when to stop mixing the ingredients based on the amount of power supplied to the mixer motor 95.

In the embodiment shown in FIG. 2, the mixing-time controller 85, or a component of the mixing-time controller (e.g., a processor), includes data ports. The data ports allow the mixing-time controller 85 to communicate with other devices. In FIG. 2, the mixing-time controller 85 is coupled with a computer 115. The mixing-time controller 85 may include data input ports and data output ports to send and receive data from the computer 115. For example, the mixing-time controller 85 may send power-level data to the computer 115 to be read, stored and analyzed. The mixing-time controller 85 may receive data from the computer 115 relating to control algorithms. In other embodiments, the mixing-time controller may be coupled to a remote network.

In still other embodiments, a farinograph, test mixer, or other dough-characteristic detector is used on a sample of each pallet of doughnut mix that arrives in a central location. Then, a cover sheet describing the characteristics of the mix, the proper percentage or amount of water that should be added, and the time period for which the doughnut mix should be mixed in a mixing machine in order to provide a guideline for the end user. Each pallet, with a cover sheet, would then be shipped to a retail store for use. At the retail store, the end users would use the cover sheet to guide them in the mixing of the doughnut mix.

In an alternative embodiment, the mixer motor may include a transmission and/or a clutch between the motor and the mixing apparatus (e.g., between the motor and the dough hook or agitators). The mixing-time controller may include a switch for disengaging the clutch or otherwise halting the mixing apparatus to stop dough mixing. The processor and other aspects of this alternative embodiment operate as discussed above. When the timer expires, the switch operates to disengage the clutch between the motor and the mixing apparatus, thus halting the mixing apparatus from operating.

Those of ordinary skill in the art will recognize that the invention described herein is not limited to application in yeast-raised doughnut mixers as described herein. The production of other types of products, e.g., cakes, honey buns, and pie mix, may be carried out in accordance with the present invention. The manufacturers or users of embodiments of the invention in such applications may adjust the algorithm, the timer period, and other aspects of measurement of peak and shut-off time to produce a desirable product.

The following discussion relates to how a control algorithm for use in the present invention may be developed. In developing the proper algorithm for use in actual mixing, it is helpful to use a farinograph. A farinograph provides characteristics of flour after testing of the subject flour. Characteristics such as peak time, arrival time, and stability may be determined. A farinograph can generate a power curve (a curve showing power (e.g., amps) used by the mixer motor vs. time) and it may be useful to compare the power curve shown on a farinograph to the power curve in using a doughnut mixing machine.

The power spikes, slope, and other characteristics may be observed in the farinograph power curve in order to develop an effective algorithm for use in the actual mixing machines. In doing so, it is very helpful to determine the relationship between the characteristics provided by a farinograph and the characteristics of an actual mixing on a doughnut mixing machine. A lab mixer is also useful in experimenting with embodiments of the present invention and determining a useful algorithm and timing periods.

FIG. 3 is a sample graph showing mixer motor power use versus time as output from a laboratory mixer. Similar graphs may be generated by a system of the present invention for mixing dough ingredients that is coupled to a computer or computer network. FIG. 3 shows mixer motor power use on the y axis and time on the x axis. A New Universal Power Cell (the power meter) was used in conjunction with embodiments of the present invention in assisting the gathering of the data shown in FIG. 3. This type of power cell includes analog outputs that range from 0–10 Volts DC, and this output is read by the data gathering device used, stored in a computer, and graphed as shown in FIG. 3. The analog output from the power cell reflects the power use of the mixer motor. The DC voltage of the outputs of the power cell corresponds to the power use of the mixer motor and is graphed in FIG. 3.

The y axis is voltage, and corresponds to horsepower (corresponding generally to 0–3.5 HP), or power, used by the mixer motor. The x axis is time. In FIG. 3, data point numbers are shown on the x axis (e.g., data point number 7489). The data points were gathered every tenth of a second (ten times per second). Thus, the data point numbers may be converted to time (in minutes) by dividing the data point number by 600. The curve shown in FIG. 3 is a sixth degree polynomial designed to fit the actual data.

FIG. 3 is intended to provide the reader with a view of experimentation that is helpful in developing the algorithm and other aspects of the present invention. For example, a farinograph may be used to generate numerous graphs for a particular shipment of flour. These graphs may be used to develop parameters associated with this particular shipment of flour to be used in the control algorithm. These parameters can be included with the other shipping information sent with the flour. The recipient of the flour can modify the control algorithm in the dough mixing system. The control algorithms in the dough mixing systems at each location to receive the flour may also be modified from a single location using a computer network.

The graphs may also be used to develop other control algorithms to identify the point at which the power supplied to the mixer motor declines. In FIG. 3, the power supplied to the mixer motor declines after approximately twelve and one-half minutes of mixing.

Various embodiments of the invention have been described in fulfillment of the various objects of the invention. It should be recognized that these embodiments are merely illustrative of the principles of the present invention. Numerous modifications and adaptations thereof will be apparent to those skilled in the art without departing from the spirit and scope of the present invention.

That which is claimed:

1. A mixing system for dough ingredients, comprising:
   a mixing device;
   a motor coupled to the mixing device;
   a power source adapted to provide power to the motor;
   a power meter positioned between the motor and the power source;
   a switch positioned between the motor and the power source;
   a processor in communication with the power meter; and a timer in communication with the processor and the switch;

wherein the power meter and the processor are adapted to identify a decline in the amount of power supplied to the mixer during mixing and wherein the processor, the timer, and the switch are adapted to allow mixing to continue for a predetermined period of time after identification of the decline in the amount of power supplied.

2. The mixing system of claim 1, wherein the mixing device is selected from the group consisting of at least one dough hook, at least one agitator, at least one paddle and at least one spoon.

3. The mixing system of claim 1, further comprising a transmission coupled to the motor.

4. The mixing system of claim 3, further comprising a clutch coupled to the motor.

5. The mixing system of claim 1, further comprising a clutch coupled to the motor.

6. The mixing system of claim 1, further comprising a mixing rod coupled to the motor.

7. The mixing system of claim 1, wherein the power meter and the switch are connected in series between the power source and the motor.

8. The mixing system of claim 1, wherein the processor receives data from the power meter relating to an amount of power supplied to the motor at specified time intervals.

9. The mixing system of claim 8, wherein the processor comprises memory allowing the processor to store the data from the power meter.

10. The mixing system of claim 1, wherein the processor comprises at least one data input port.

11. The mixing system of claim 1, wherein a first data input port receives data from the power meter relating to an amount of power supplied to the mixer at specified time intervals.

12. The mixing system of claim 11, wherein a second data input port receives signals from a computer.

13. The mixing system of claim 11, wherein a second data input port receives signals from a computer network.

14. The mixing system of claim 1, wherein the processor comprises at least one data output port.

15. The mixing system of claim 14, wherein a first data output port is coupled with the timer.

16. The mixing system of claim 15, wherein a second data output port is coupled with a computer.

17. The mixing system of claim 1, wherein the processor is coupled with a computer or a computer network.

18. A mixing system for dough ingredients, comprising:

means for mixing dough ingredients with a mixing device;

means for measuring an amount of power supplied to the mixing device;

means for identifying a decline in the amount of power supplied to the mixing device; and means for ceasing mixing after a predetermined period of time after identification of the decline in the amount of power supplied.

19. The mixing system of claim 18, further comprising means for storing data related to the amount of power supplied at specified time intervals.

20. A mixing system for dough ingredients, comprising:

a mixing device;

a motor coupled to the mixing device;

a power source adapted to provide power to the motor;

a power meter positioned between the motor and the power source;

a switch positioned between the motor and the power source; and a processor comprising a timer, the processor being adapted for communication with the power meter and the switch;

wherein the power meter and the processor are adapted to identify a decline in the amount of power supplied to the mixer during mixing and wherein the processor and the switch are adapted to allow mixing to continue for a predetermined period of time after identification of the decline in the amount of power supplied.

* * * * *